United States Patent [19]

Sirrenberg et al.

[11] 4,140,787

[45] Feb. 20, 1979

[54] COMBATING ARTHROPODS WITH 1-[HALOALKYL-PHENYL)-CARBAMOYL]-3-(4-HALOPHENYL)-2-PYRAZOLINES

[75] Inventors: Wilhelm Sirrenberg, Sprockhoevel; Erich Klauke, Odenthal; Ingeborg Hammann, Cologne; Wilhelm Stendel, Wuppertal, all of Fed. Rep. of Germany

[73] Assignee: Bayer Aktiengesellschaft, Leverkusen, Fed. Rep. of Germany

[21] Appl. No.: 861,740

[22] Filed: Dec. 19, 1977

[30] Foreign Application Priority Data

Jan. 5, 1977 [DE] Fed. Rep. of Germany ....... 2700288

[51] Int. Cl.² ..................... A01N 9/22; C07D 231/06
[52] U.S. Cl. ................................. 424/273 P; 548/379
[58] Field of Search ...................... 548/329; 424/273 P

[56] References Cited

U.S. PATENT DOCUMENTS

| 3,991,073 | 11/1976 | Mulder et al. ..................... 424/248.5 |
| 4,010,271 | 3/1977 | Mulder et al. ..................... 424/273 P |
| 4,070,365 | 1/1978 | van Daalen et al. ............... 424/273 P |

OTHER PUBLICATIONS

Philips, Chem. Abst., 1975, vol. 82, No. 43411v.
Weber et al., Chem. Abst., 1972, vol. 77, No. 101452u.

*Primary Examiner*—Natalie Trousof
*Assistant Examiner*—Natalia Harkaway
*Attorney, Agent, or Firm*—Sprung, Felfe, Horn, Lynch & Kramer

[57] ABSTRACT

1-[(Haloalkyl-phenyl)-carbamoyl]-3-(4-halophenyl)-2-pyrazolines of the formula

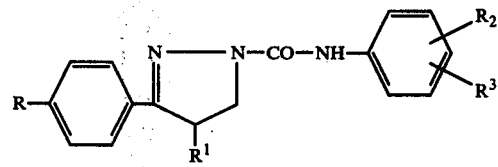

in which
R is halogen,
$R^1$ is hydrogen or alkyl,
$R^2$ is hydrogen or halogen, and
$R^3$ is halogenoalkyl
which possess arthropodicidal properties.

7 Claims, No Drawings

COMBATING ARTHROPODS WITH 1-[HALOALKYL-PHENYL)-CARBAMOYL]-3-(4-HALOPHENYL)-2-PYRAZOLINES

The present invention relates to and has for its objects the provision of particular new 1-[(haloalkyl-phenyl)-carbamoyl]-3-(4-halophenyl)-2-pyrazolines which possess arthropodicidal properties, active compositions in the form of mixtures of such compounds with solid and liquid dispersible carrier vehicles, and methods for producing such compounds and for using such compounds in a new way especially for combating pests, e.g. arthropods, with other and further objects becoming apparent from a study of the within specification and accompanying examples.

It is already known that phenylcarbamoyl-monophenyl- and -diphenyl-pyrazolines, for example 1-(4-chlorophenyl-carbamoyl)-3-(4-chlorophenyl)-, 1-(4-chlorophenylcarbamoyl)-3-(4-chlorophenyl)-4-methyl- and 1-(4-chlorophenylcarbamoyl)-3,5-bis-(4-chlorophenyl)-2-pyrazoline, are distinguished by an insecticidal activity (see, for example, German Offenlegungsschriften (German Published Specifications) Nos. 2,304,584 and 2,529,689).

The present invention now provides, as new compounds, the phenylcarbamoyl-pyrazolines of the general formula

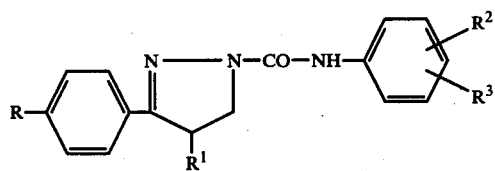

in which
R represents halogen,
R¹ represents hydrogen or alkyl,
R² represents hydrogen or halogen and
R³ represents haloalkyl.

Preferably, R represents chlorine or bromine, R¹ represents hydrogen or straight-chain or branched alkyl with 1 to 3 carbon atoms (especially methyl), R² represents hydrogen or chlorine and R³ represents monochlorodifluoromethyl, dichloromonofluoromethyl, monofluoromethyl or difluoromethyl.

Surprisingly, the phenylcarbamoyl-pyrazolines according to the invention exhibit a better insecticidal action than the corresponding phenylcarbamoyl-monophenyl- and -diphenyl-pyrazolines of analogous structure and of the same type of action. The products according to the present invention thus represent a genuine enrichment of the art.

The invention also provides a process for the preparation of a pyrazoline of the formula (I), in which a 3-halophenyl-2-pyrazoline of the general formula

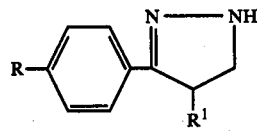

in which

R and R¹ have the above-mentioned meanings, is reacted with a phenyl isocyanate of the general formula

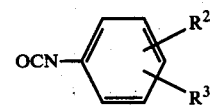

in which
R² and R³ have the above-mentioned meanings, if appropriate in the presence of a solvent or diluent.

If, for example, 3-(4-bromophenyl)-2-pyrazoline and 3-chloro-4-monochlorodifluoromethyl-phenyl isocyanate are used as starting materials, the course of the reaction can be represented by the following equation:

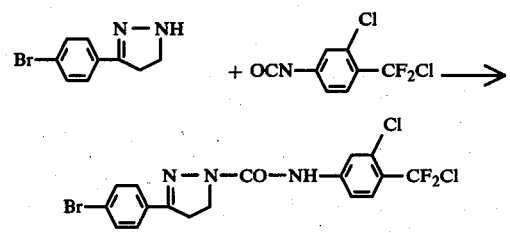

3-Halophenyl-2-pyrazolines (II) to be used as starting materials are known and can be prepared in accordance with processes known from the literature (see, for example, German Offenlegungsschrift (German Published Specification) No. 2,529,689).

The following may be mentioned individually as examples of the 3-halophenyl-2-pyrazolines: 3-(4-chlorophenyl)-2-pyrazoline, 3-(4-bromophenyl)-2-pyrazoline, 3-(4-chlorophenyl)-4-methyl-2-pyrazoline and 3-(4-bromophenyl)-4-methyl-2-pyrazoline.

Phenyl isocyanates (III) to be used as starting materials are in some cases known and can be prepared in accordance with processes known from the literature (see, for example, German Offenlegungsschrift (German Published Specification) No. 2,529,689).

The following may be mentioned individually as examples of these compounds: 4-monofluoromethyl-phenyl isocyanate, 4-difluoromethyl-phenyl isocyanate, 4-monochlorodifluoromethylphenyl isocyanate, 4-dichloromonofluoromethyl-phenyl isocyanate, 3-chloro-4-monofluoromethyl-phenyl isocyanate, 3-chloro-4-difluoromethyl-phenyl isocyanate, 3-chloro-4-monochlorodifluoromethyl-phenyl isocyanate and 3-chloro-4-dichloromonofluoro-phenyl isocyanate.

The process for the preparation of the compounds according to the invention is preferably carried out in the presence of a suitable solvent or diluent. Virtually all inert organic solvents can be used for this purpose, especially aliphatic and aromatic, optionally chlorinated, hydrocarbons, such as benzene, toluene, xylene, benzine, methylene chloride, chloroform, carbon tetrachloride and chlorobenzene; ethers, for example diethyl ether, dibutyl ether and dioxane; ketones, for example acetone, methyl ethyl ketone, methyl isopropyl ketone and methyl isobutyl ketone; and nitriles, such as acetonitrile and propionitrile.

The reaction temperature can be varied within a substantial range. In general, the reaction is carried out at from 20° to 120° C., preferably at from 50° to 90° C.

In general, the reaction is allowed to take place under normal pressure.

To carry out the process, the starting materials are preferably employed in stoichiometric amounts. An excess of one or the other component produces no significant advantages. The reaction is preferably carried out in one of the stated solvents or diluents, at an elevated temperature. After completion of the reaction, the mixture is cooled, whereupon the compounds crystallize out.

The new compounds (I) are obtained in the crystalline form and are characterized by their melting point.

As already mentioned, the carbamoyl-pyrazolines according to the invention are distinguished by an excellent insecticidal activity. They are active against insects which damage plants and, in the veterinary medicine field, against ectoparasites, such as parasitic fly larvae.

The active compounds are well tolerated by plants, have a favorable level of toxicity to warm-blooded animals, and can be used for combating arthropod pests, especially insects which are encountered in agriculture, in forestry, in the protection of stored products and of materials, and in the hygiene field. They are active against normally sensitive and resistant species and against all or some stages of development. The above-mentioned pests include:

from the class of the Isopoda, for example *Oniscus asellus, Armadillidium vulgare* and *Porcellio scaber;* from the class of the Diplopoda, for example *Blaniulus guttulatus;* from the class of the Chilopoda, for example *Geophilus carpophagus* and Scutigera spec.;

from the class of the Symphyla, for example *Scutigerella immaculata;* from the order of the Thysanura, for example *Lepisma saccharina;* from the order of the Collembola, for example *Onychiurus armatus;* from the order of the Orthoptera, for example *Blatta orientalis, Periplaneta americana, Leucophaea maderae, Blattella germanica, Acheta domesticus,* Gryllotalpa spp., *Locusta migratoria migratorioides, Melanoplus differentialis* and *Schistocerca gregaria;* from the order of the Dermaptera, for example *Forficula auricularia;* from the order of the Isoptera, for example Reticulitermes spp.;

from the order of the Anoplura, for example *Phylloxera vastatrix,* Pemphigus spp., *Pediculus humanus corporis,* Haematopinus spp. and Linognathus spp.;

from the order of the Mallophaga, for example Trichodectes spp. and Damalinea spp.;

from the order of the Thysanoptera, for example *Hercinothrips femoralis* and *Thrips tabaci;* from the order of the Heteroptera, for example Eurygaster spp., *Dysdercus intermedius, Piesma quadrata, Cimex lectularius, Rhodnius prolixus* and Triatoma spp.;

from the order of the Homoptera, for example *Aleurodes brassicae, Bemisia tabaci, Trialeurodes vaporariorum, Aphis gossypii, Brevicoryne brassicae, Cryptomyzus ribis, Doralis fabae, Doralis pomi, Eriosoma lanigerum, Hyalopterus arundinis, Macrosiphum avenae,* Myzus spp., *Phorodon humuli, Rhopalosiphum padi, Empoasca spp., Euscelis bilobatus, Nephotettix cincticeps, Lecanium corni, Saissetia oleae, Laodelphax striatellus, Nilaparvata lugens, Aonidiella aurantii, Aspidiotus hederae,* Pseudococcus spp. and Psylla spp.;

from the order of the Lepidoptera, for example *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spp., *Bucculatrix thurberiella, Phyllocnistis citrella,* Agrotis spp., Euxoa spp., Feltia spp., *Earias insulana,* Heliothis spp., *Laphygma exigua, Mamestra brassicae, Panolis flammea, Prodenia litura,* Spodoptera spp., *Trichoplusia ni, Carpocapsa pomonella,* Pieris spp., Chilo spp., *Pyrausta nubilalis, Ephestia kuehniella, Galleria mellonella, Cacoecia podana, Capua reticulana, Choristoneura fumiferana, Clysia ambiguella, Homona magnanima* and *Tortrix viridana;* from the order of the Coleoptera, for example *Anobium punctatum, Rhizopertha dominica, Bruchidius obtectus, Acanthoscelides obtectus, Hylotrupes bajulus, Agelastica alni, Leptinotarsa decemlineata, Phaedon cochleariae,* Diabrotica spp., *Psylliodes chrysocephala, Epilachna varivestis,* Atomaria spp., *Oryzaephilus surinamensis,* Anthonomus spp., Sitophilus spp., *Otiorrhynchus sulcatus, Cosmopolites sordidus, Ceuthorrhynchus assimilis, Hypera postica,* Dermestes spp., Trogoderma spp., Anthrenus spp., Attagenus spp., Lyctus spp., *Meligethes aeneus,* Ptinus spp., *Niptus hololeucus, Gibbium psylloides,* Tribolium spp., *Tenebrio molitor,* Agriotes spp., Conoderus spp., *Melolontha melolontha, Amphimallon solstitialis* and *Costelytra zealandica;* from the order of the Hymenoptera, for example Diprion spp., Hoplocampa spp., Lasius spp., *Monomorium pharaonis* and Vespa spp.;

from the order of the Diptera, for example Aedes spp., Anopheles spp., Culex spp., *Drosophila melanogaster,* Musca spp., Fannia spp., *Calliphora erythrocephala,* Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit,* Phorbis spp., *Pegomyia hyoscyami, Ceratitis capitata, Dacus oleae* and *Tipula paludosa;* from the order of the Siphonaptera, for example *Xenopsylla cheopis* and Ceratophyllus spp.

The active compounds according to the instant invention can be utilized, if desired, in the form of the usual formulations or compositions with conventional inert (i.e. plant compatible or herbicidally inert) pesticide diluents or extenders, i.e. diluents, carriers or extenders of the type usable in conventional pesticide formulations or compositions, e.g. conventional pesticide dispersible carrier vehicles such as gases, solutions, emulsions, wettable powders, suspensions, powders, dusting agents, foams, pastes, soluble powders, granules, aerosols, suspension-emulsion concentrates, seed-treatment powders, natural and synthetic materials impregnated with active compound, very fine capsules in polymeric substances and in coating compositions, for use on seed, and formulations used with burning equipment, such as fumigating cartridges, fumigating cans, fumigating coils and the like, as well as ULV cold mist and warm mist formulations.

These are prepared in known manner, for instance by extending the active compounds with conventional pesticide dispersible liquid diluent carriers and/or dispersible solid carriers optionally with the use of carrier vehicle assistants, e.g. conventional pesticide surface-active agents, including emulsifying agents and/or dispersing agents, whereby, for example, in the case where water is used as diluent, organic solvents may be added as auxiliary solvents. The following may be chiefly considered for use as conventional carrier vehicles for this purpose: aerosol propellants which are gaseous at normal temperatures and pressures, such as halogenated hydrocarbons, e.g. dichlorodifluoromethane and trichloromethane, as well as butane, propane, nitrogen and carbon dioxide; inert dispersible liquid diluent carriers, including inert organic solvents, such as aromatic hydrocarbons (e.g. benzene, toluene, xylene, alkyl naphthalenes, etc.), halogenated, especially chlorinated, aromatic hydrocarbons (e.g. chlorobenzenes, etc.), cycloalkanes, (e.g. cyclohexane, etc.), paraffins (e.g. petroleum or mineral oil fractions), chlorinated aliphatic hydrocarbons (e.g. methylene chloride, chloroethylenes, etc.), alcohols (e.g. methanol, ethanol, propanol, butanol, glycol, etc.) as well as ethers and esters thereof (e.g. glycol monomethyl ether, etc.), amines (e.g. ethanolamine, etc.), amides (e.g. dimethyl formamide, etc.), sulfoxides (e.g. dimethyl sulfoxide, etc.), acetonitrile, ketones (e.g. ketone, methyl ethyl ketone methyl isobutyl ketone, cyclohexanone, etc.), and/or water; as solid carriers, ground natural minerals, such as kaolins, clays, talc, chalk, quartz, attapulgite, montmorillonite or diatomaceous earth, and ground synthetic minerals, such as highly-dispersed silicic acid, alumina and silicates; as solid carriers for granules; crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; whereas the following may be chiefly considered for use as conventional carrier vehicle assistants, e.g. surface-active agents, for this purpose: emulsifying agents, such as non-ionic and/or anionic emulsifying agents (e.g. polyethylene oxide esters of fatty acids, polyethylene oxide ethers of fatty alcohols, alkyl sulfates, alkyl sulfonates, aryl sulfonates, albumin hydrolyzates, etc., and especially alkyl arylpolyglycol ethers, magnesium stearate, sodium oleate, etc.); and/or dispersing agents, such as lignin, sulfite waate liquors, methyl cellulose, etc.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

Such active compounds may be employed alone or in the form of mixtures with one another and/or with such solid and/or liquid dispersible carrier vehicles and/or with other known compatible active agents, especially plant protection agents, such as other arthropodicides, or nematicides, fungicides, bactericides, rodenticides, herbicides, fertilizers, growth-regulating agents, etc., if desired, or in the form of particular dosage preparations for specific application made therefrom, such as solutions, emulsions, suspensions, powders, pastes, and granules which are thus ready for use.

As concerns commercially marketed preparations, these generally contemplate carrier composition mixtures in which the active compound is present in an amount substantially between about 0.1-95% by weight, and preferably 0.5-90% by weight, of the mixture, whereas carrier composition mixtures suitable for direct application or field application generally contemplate those in which the active compound is present in an amount substantially between about 0.0000001-100, preferably 0.01-10%, by weight of the mixture. Thus, the present invention contemplates overall compositions which comprise mixtures of a conventional dispersible carrier such as (1) a dispersible inert finely divided carrier solid, and/or (2) a dispersible carrier liquid such as an inert organic solvent and/or water, preferably including a surface-active effective amount of a carrier vehicle assistant, e.g. a surface-active agent, such as an emulsifying agent and/or a dispersing agent, and an amount of the active compound which is effective for the purpose in question and which is generally between about 0.0001-95%, and preferably 0.01-95%, by weight of the mixture.

The active compounds can also be used in accordance with the well known ultra-low-volume process with good success, i.e. by applying such compound if normally a liquid, or by applying a liquid composition containing the same, via very effective atomizing equipment, in finely divided form, e.g. average particle diameter of from 50-100 microns, or even less, i.e. mist form, for example by airplane crop spraying techniques. Only up to at most about a few liters/hectare are needed, and often amounts only up to about 15 to 1000 g/hectare, preferably 40 to 600 g/hectare, are sufficient. In this process it is possible to use highly concentrated liquid compositions with said liquid carrier vehicles containing from about 20 to about 95% by weight of the active compound or even the 100% active substance alone, e.g. about 20-100% by weight of the active compound.

In the veterinary field, the active compounds according to the invention may be used in a known manner, such as orally in the form of, for example, tablets, capsules, drenches and granules; dermally by means of, for example, dipping, spraying, pouring-on, spotting-on and powdering; and parenterally, for example by means of injections.

Furthermore, the present invention contemplates methods of selectively killing, combating or controlling pests, e.g. arthropods, which comprises applying to at least one of correspondingly (a) such arthropods, and (b) the corresponding habitat thereof, i.e. the locus to be protected, e.g. to a growing crop, to an area where a crop is to be grown or to a domestic animal, a correspondingly combative or toxic amount, i.e. an arthropodicidally effective amount, of the particular active compound of the invention alone or together with a carrier vehicle as noted above. The instant formulations or compositions are applied in the usual manner, for instance by spraying, atomizing, vaporizing, scattering, dusting, watering, squirting, sprinkling, pouring, fumigating, dry dressing, moist dressing, wet dressing, slurry dressing, encrusting, and the like.

It will be realized, of course, that the concentration of the particular active compoun utilized in admixture with the carrier vehicle will depend upon the intended application. Therefore, in special cases it is possible to go above or below the aforementioned concentration ranges.

The preparation of the new compounds of the present invention is illustrated, without limitation, by the following examples:

EXAMPLE 1

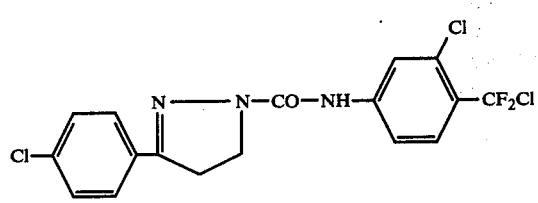

11.9 g (0.05 mol) of 3-chloro-4-monochlorodifluoromethyl-phenyl isocyanate in 20 ml of toluene were added, at 60° C., to a solution of 9 g (0.05 mol) of 3-(4-chlorophenyl)-2-pyrazoline in 60 ml of toluene. The batch was stirred for 2 hours at 80° C. After the reaction solution had cooled, the desired compound crystallized out, and after filtering it off, 10.8 g (51.5% of theory) of 1-[(3-chloro-4-monochlorodifluoromethyl-phenyl)-carbamoyl]-3-(4-chlorophenyl)-2-pyrazoline having a melting point of 197° C. were obtained. The yield was not optimized.

The following compounds were synthesized analogously:

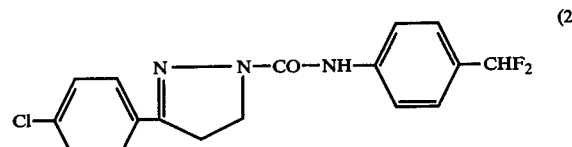

melting point: 170° C

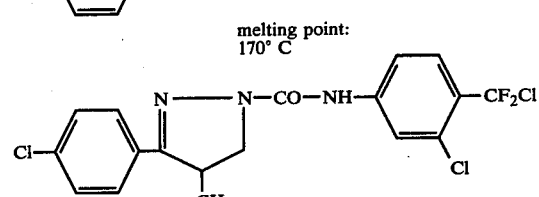

melting point: 132–133° C

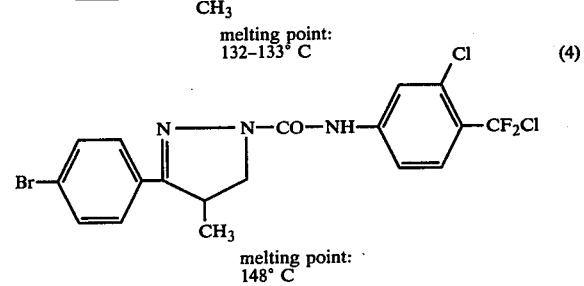

melting point: 148° C

The insecticidal activity of the compounds of this invention is illustrated by the following examples wherein the compounds according to the present invention are each identified by the number (given in brackets) from the preparative example hereinabove.

The known comparison compounds are identified as follows:

(A) =

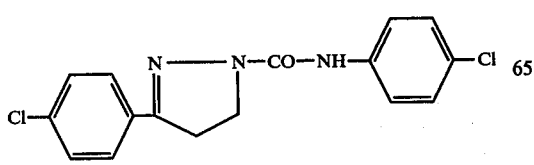

(B) =

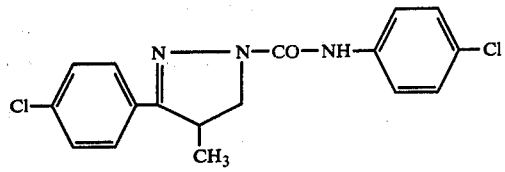

(C) =

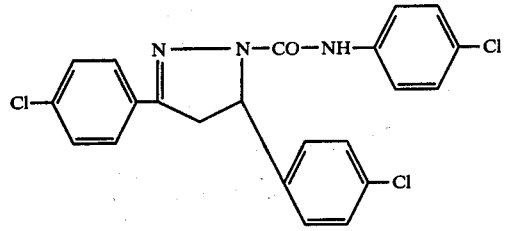

EXAMPLE 2

Phaedon larvae test
Solvent: 3 parts by weight of dimethylformamide
Emulsifier: 1 part by weight of alkylaryl polyglycol ether To produce a suitable preparation of active compound, 1 part by weight of the active compound was mixed with the stated amount of solvent containing the stated amount of emulsifier and the concentrate was diluted with water to the desired concentration.

Cabbage leaves (*Brassica oleracea*) were sprayed with the preparation of the active compound until dripping wet and were then infested with mustard beetle larvae (*Phaedon cochleariae*).

After the specified periods of time, the degree of destruction was determined in %: 100% meant that all of the beetle larvae had been killed whereas 0% meant that none of the beetle larvae had been killed.

The active compounds, the concentrations of the active compounds, the evaluation times and the results can be seen from the following table:

Table 1

| Active compounds | (insects which damage plants) Phaedon larvae test | |
|---|---|---|
| | Active compound concentration in % | Degree of destruction in % after 4 days |
| (A) | 0.01 | 100 |
| | 0.001 | 50 |
| | 0.0001 | 0 |
| (B) | 0.01 | 100 |
| | 0.001 | 20 |
| | 0.0001 | 0 |
| (C) | 0.01 | 100 |
| | 0.001 | 0 |
| (2) | 0.01 | 100 |
| | 0.001 | 85 |
| | 0.0001 | 50 |
| (1) | 0.01 | 100 |
| | 0.001 | 100 |
| | 0.0001 | 75 |
| (3) | 0.01 | 100 |
| | 0.001 | 100 |
| | 0.0001 | 60 |

EXAMPLE 3

Laphygma test

Solvent: 3 parts by weight of dimethylformamide
Emulsifier: 1 part by weight of alkylaryl polyglycol ether To produce a suitable preparation of active compound, 1 part by weight of the active compound was mixed with the stated amount of solvent and the stated amount of emulsifier and the concentrate was diluted with water to the desired concentration.

Cotton leaves (*Gossypium hirsutum*) were sprayed with the preparation of the active compound until dew-moist and were then infested with caterpillars of the owlet moth (*Laphygma exigua*).

After the specified periods of time, the destruction in % was determined. 100% meant that all of the caterpillars had been killed whereas 0% indicated that none of the caterpillars had been killed.

The active compounds, the concentrations of the active compounds, the evaluation times and the results can be seen from the following table:

Table 2

| | (insects which damage plants) Laphygma test | |
|---|---|---|
| Active compounds | Active compound concentration in % | Degree of destruction in % after 4 days |
| (C) | 0.1 | 100 |
| | 0.01 | 80 |
| | 0.001 | 0 |
| (4) | 0.1 | 100 |
| | 0.01 | 100 |
| | 0.001 | 70 |

EXAMPLE 4

Test with parasitic fly larvae

Emulsifier: 80 parts by weight of castor oil polyglycol ether

To produce a suitable preparation of active compound, 20 parts by weight of active compound were mixed with the stated amount of the emulsifier and the mixture thus obtained was diluted with water to the desired concentration.

About 20 fly larvae (*Lucilia cuprina*, resistant) were introduced into a test tube which contained about 3 ml of a 20% strength egg-yolk-powder suspension in water and which was fitted with a cottonwool plug of appropriate size. 0.5 ml of the active compound preparation were placed on this egg-yolk-powder suspension. After 24 hours, the degree of destruction in % was determined. 100% meant that all of the larvae had been killed and 0% meant that none of the larvae had been killed.

The active compounds, active compound concentrations and degree of destruction can be seen from the table which follows:

Table 3

| | Test with parasitic fly larvae | |
|---|---|---|
| Active compound | Active compound concentration in ppm | Destructive action in % |
| (3) | 1000 | 100 |
| | 300 | 100 |
| | 100 | 100 |
| (4) | 1000 | 100 |
| | 100 | 100 |

It will be appreciated that the instant specification and examples are set forth by way of illustration and not limitation, and that various modifications and changes may be made without departing from the spirit and scope of the present invention.

What is claimed is:

1. A 1-[(haloalkyl-phenyl)-carbamoyl]-3-(4-halophenyl)-2-pyrazoline of the formula

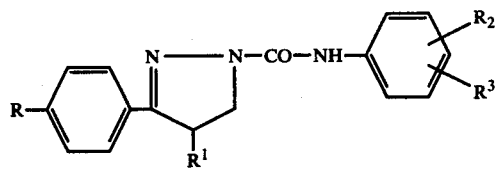

in which
R is halogen,
R¹ is hydrogen or alkyl with 1 to 3 carbon atoms,
R² is hydrogen or halogen, and
R³ is monochlorodifluoromethyl, dichloromonofluoromethyl, monofluoromethyl or difluoromethyl.

2. A compound according to claim 1, in which
R is chlorine or bromine, and
R² is hydrogen or chlorine.

3. A compound according to claim 1, wherein such compound is 1-[(3-chloro-4-monochlorodifluoromethylphenyl)-carbamoyl]-3-(4-chlorophenyl)-2-pyrazoline of the formula

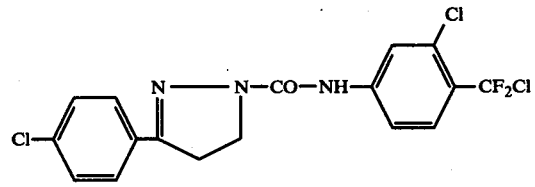

4. A compound according to claim 1, wherein such compound is 1-[(4-difluoromethyl-phenyl)-carbamoyl]-3-(4-chlorophenyl)-2-pyrazoline of the formula

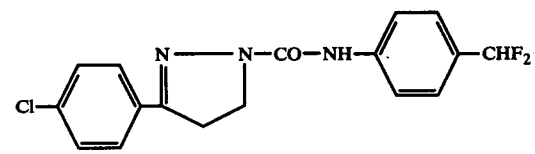

5. A compound according to claim 1, wherein such compound is 1-[(3-chloro-4-monochlorodifluoromethylphenyl)-carbamoyl]-4-methyl-3-(4-chlorophenyl)-2-pyrazoline of the formula

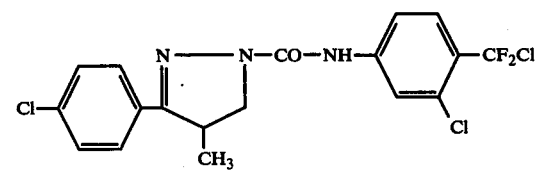

6. A compound according to claim 1, wherein such compound is 1-[(3-chloro-4-monochlorodifluoromethylphenyl)-carbamoyl]-4-methyl-3-(4-bromophenyl)-2-pyrazoline of the formula

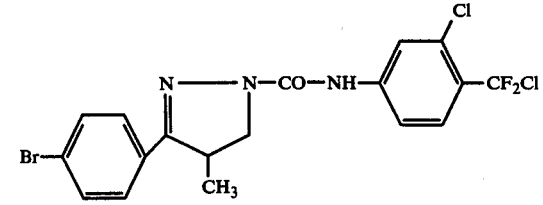

7. An arthropodicidal composition containing as active ingredient an arthropodicidally effective amount of a compound according to claim 1 in admixture with a diluent.

* * * * *